(12) United States Patent
Burgess

(10) Patent No.: US 7,402,677 B2
(45) Date of Patent: Jul. 22, 2008

(54) FLUORESCENT THROUGH-BOND ENERGY TRANSFER CASSETTES BASED ON XANTHINE AND PYRONIN DERIVATIVES

(75) Inventor: Kevin Burgess, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 454 days.

(21) Appl. No.: 10/876,919

(22) Filed: Jun. 25, 2004

(65) Prior Publication Data

US 2005/0032120 A1     Feb. 10, 2005

Related U.S. Application Data

(60) Provisional application No. 60/482,483, filed on Jun. 25, 2003.

(51) Int. Cl.
| | | |
|---|---|---|
| C07D 293/00 | (2006.01) | |
| C07D 209/56 | (2006.01) | |
| C07D 209/02 | (2006.01) | |
| G03C 1/005 | (2006.01) | |
| C07H 19/04 | (2006.01) | |
| G01N 33/533 | (2006.01) | |

(52) U.S. Cl. ............... 548/100; 548/427; 548/455; 430/581; 536/26.6; 436/546
(58) Field of Classification Search ............ 548/100, 548/427, 455; 430/581; 536/26.6; 436/546
See application file for complete search history.

(56) References Cited

U.S. PATENT DOCUMENTS

| | | | |
|---|---|---|---|
| 5,945,526 A | 8/1999 | Lee et al. ............. | 536/26.6 |
| 6,335,440 B1 * | 1/2002 | Lee et al. ............. | 536/26.6 |
| 6,340,750 B1 * | 1/2002 | Burgess et al. ........ | 536/26.6 |

OTHER PUBLICATIONS

International Search report and Written Opinion; PCT/US04/20236; p. 7, Jun. 19, 2006.
Jiao et al.; "Sythesis of Regioisomerically Pure 5- or 6-Halogenated Flouresceins"; Journal of Organic Chemistry, vol. 68, pp. 8264-8267, 2003.
Jiao et al.; "Fluorescent, Through-Bond Energy Transfer Cassettes for Labeling Multiple Biological Molecules in One Experiment"; Journal of American Chemical Society, vol. 125, pp. 14668-14669, 2003.
Jiao et al.; "Microwave-Assisted Synthesis of Regioisomerically Pure Bromorhodamine Derivatives"; Organic Letters, vol. 5, No. 2, pp. 3675-3677, 2003.
Han et al.; "Microwave-Assisted Functionalization of Bromo-Fluorescein and Bromorhodamine Derivatives"; Tetrahedron Letters, vol. 44, pp. 9359-9362, 2003.
Smith et al.; "Fluorescence Detection in Automated DNA Sequence Analysis"; Nature, vol. 321, pp. 674-679, Jun. 12, 1986.
R.M. Clegg; "Fluorescence Resonance Energy Transfer"; Current Opinion in Biotechnology, vol. 6, pp. 103-110, 1995.

(Continued)

Primary Examiner—Jezia Riley
(74) Attorney, Agent, or Firm—Baker Botts L.L.P.

(57) ABSTRACT

A TBET cassette including at least one xanthine- or pyronin-based compound as a donor or acceptor is disclosed. Also, a method of TBET cassette design in which four criteria may be used is provided. TBET cassettes may be used to label biological molecules, in clothing dyes, and in cosmetics.

10 Claims, 4 Drawing Sheets

OTHER PUBLICATIONS

Wu et al.; "Resonance Energy Transfer; Methods and Applications"; Analytical Biochemistry, vol. 218, pp. 1-13, 1994.

Speiser; "Photophysics and Mechnisms of Intramolecular Electronic Energy Transfer in Bichromophoric Molecular Systems: Solution and Supersonic Jet Studies"; Chemical Reviews, vol. 96, pp. 1953-1976, 1996.

Sonogashira et al.; "A Convenient Synthesis of Acetylenes: Catalytic Substitutions of Acetylenic Hydrogen With Bromoalkenes, Iodarenes, and Bromopyridines"; tetrahedron Letters, No. 50, pp. 4467-4470, 1975.

Bunz; "Poly(aryleneethynylene)s: Syntheses, Properties, Structures, and Applications"; Chemical Reviews, vol. 100, pp. 1605-1644, 2000.

Burghart et al.; "Energy Transfer Cassettes Based on BODIPY Dyes"; Chem. Commun., p. 2, 2000.

Darrell D. Ebbing et al., "Molecular Geometry and Chemical Bonding Theory, Valence Bond Theory"; General Chemistry Sixth Edition; Chapter 10; pp. 409-419, 1999.

* cited by examiner (OR SIMILAR)

(OR SIMILAR)

TYPICAL CASSETTE STRUCTURES

US 7,402,677 B2

FLUORESCENT THROUGH-BOND ENERGY TRANSFER CASSETTES BASED ON XANTHINE AND PYRONIN DERIVATIVES

PRIORITY CLAIM

The present application claims priority to U.S. Provisional Patent Application Ser. No. 60/482,483, filed Jun. 25, 2003, entitled "Fluorescent Through-Bond Energy Transfer Cassettes".

FIELD OF THE INVENTION

The present invention relates to chemical compounds able to transfer energy through their bonds and thereby fluoresce. Specifically, it relates to such compounds that are based on xanthine or pyronin.

BACKGROUND

When two fluorescent or molecular entities are joined together to form one molecule, they may, in some cases function as "energy transfer cassettes". Molecules that act as energy transfer cassettes are characterized by transfer of all or part of the energy absorbed by one of the otherwise fluorescent parts to the other, which then fluoresces with enhanced brightness. The molecular fragment that absorbs energy then donates it to the other part may be referred to as the donor, while the molecular fragment that collects energy from the donor and emits with enhanced fluorescence is typically called the acceptor.

There are various mechanisms by which a donor entity may transfer energy to an acceptor entity in the same molecule. Most frequently, the energy is transferred almost exclusively through space via a mechanism often referred to as Förster energy transfer. Energy transfer cassettes based on through-space energy transfer are extremely common.

Through-bond energy-transfer (hereafter, TBET) cassettes are rarer than through-space energy-transfer cassettes (TSET). Nevertheless, some examples have been described. The most notable ones include models for photosynthetic systems, various studies on polymeric or oligomeric systems for new materials, and other model studies featuring boron dipyrromethane dyes.

SUMMARY OF THE INVENTION

The present invention relates to TBET cassettes including a donor and an acceptor and optionally a linker. Such cassettes absorb light (or other electromagnetic energy) at a wavelength determined by the donor, acceptor and linker, if present, this energy may be transferred through bonds to the acceptor. The acceptor emits electromagnetic energy at a longer wavelength (i.e. it fluoresces). This emission wavelength is largely a function of the acceptor alone.

TBET cassettes offer clear advantages over TSET cassettes insofar as the emission wavelengths are not restricted by the Förster energy transfer mechanism. Förster energy transfer relies on close proximity of the donor and acceptor parts, and on overlap of the donor fluorescence spectrum with the acceptor absorbance spectrum. These constraints do not necessarily apply to TBET. Consequently, the donor-acceptor parts in cassettes that function predominantly via TBET can be arranged differently than cassettes that feature exclusively TSET. Further, for a given donor entity, the range of acceptors that could potentially be used is greater. This is extremely useful in multiplexing and in other applications.

The invention additionally includes a method of designing TBET cassettes. This method may include four criteria: (i) the donor and acceptor could become π-conjugated, but are prevented from doing so in the ground state by one or more twists; (ii) the TBET cassette has a significant molar extinction coefficient at the excitation wavelength; (iii) the acceptor emits with a high quantum yield at the observation wavelength; and (iv) the TBET cassette lacks functional groups that facilitate loss of fluorescence through non-radiative decay. According to some embodiments of the invention, a functional TBET cassette has all four of the foregoing properties.

The invention additionally includes methods of using TBET cassettes of the present invention, for example, as labels for biological molecules.

BRIEF DESCRIPTION OF THE DRAWINGS

Some embodiments of the present disclosure may be understood through the appended description, taken in conjunction with the following drawings in which.

DETAILED DESCRIPTION

Figure 1A:
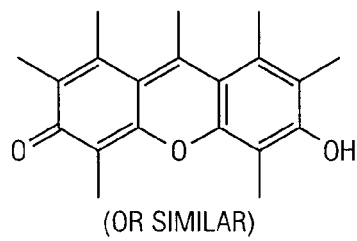
FIG. 1A illustrates xanthine-derived compounds, according to certain embodiments of the present invention.

In some embodiments, donor and acceptor fragments are connected by linkers with extended π-systems, or are directly connected (no linkers), such that electronic conjugation between the donor and acceptor systems could occur if they were made planar. If the two compounds maintain discrete donor and acceptor components (i.e., the π-systems do not simply merge to form one extended, conjugated system) then they may be called through-bond energy transfer cassettes. This name should not be taken to mean that through-space energy-transfer cannot occur as well. It simply implies that direct transfer of energy between the donor and acceptor π-systems can occur simultaneously through bonds. The precise mechanisms by which that energy transfer occurs are not fully understood.

The present invention relates to TBET cassettes including xanthine and pyronin-based compounds. Such cassettes may be similar to fluoresceine and rhodamine-like dyes. They may be used for a variety of purposes, including labeling or staining biological molecules such as proteins, polypeptides, amino acids, nucleic acids, and nucleotides.

The present invention also relates to methods of TBET cassette design for use in biological systems. Although some principles of TBET design have been described, no specific methodologies taking into account the particular constraints of biological molecules have been previously determined.

In specific examples, TBET cassettes may be designed to absorb light in one region of the spectrum and convert it to fluorescence emission at a longer wavelength. These TBET cassettes may contain donor and acceptor fragments that are able to become electronically π-conjugated with one another, but are normally prevented from doing so in the ground state by one or more twists in the conjugated system that force it to be non-planar.

The TBET cassettes may also exhibit a significant molar extinction coefficient at the wavelength(s) to be used to excite the cassettes. Generally, the donor may be selected to have a satisfactory absorbance at the wavelength to be used. The cassettes may also include an acceptor that emits fluorescence with a high quantum yield at a wavelength(s) desired for observation.

Finally, the TBET may be designed so as not to include functional groups that facilitate loss of fluorescence via non-radiative decay. Such non-radiative decay may occur at a rate competitive with the rate of energy transfer to the acceptor fragment(s) and with the rate of fluorescence. In some embodiments, the above criteria may be considered critical for TBET design.

The brightness of the fluorescence emission observed from the acceptor entity may be increased by selecting donor fragments with strong absorbance at the excitation wavelength. Emission brightness may also be increased by using more than one donor molecule per cassette.

In general, the brightness of emissions from the TBET cassette is related to the rate of energy transfer from the donor to the acceptor. Because both TBET and TSET may be operative in a TBET cassette, in some embodiments, TBET cassettes may optimize fluorescence by possessing molecular characteristics that maximize both mechanisms of energy transfer. The donor and acceptor may also be connected in an orientation that maximizes both pathways. Finally, the linker, if any may be chosen to maximize TBET.

Measurements of rates of energy transfer between donor and acceptor fragments indicate that orientations that set the two transition dipoles parallel are particularly conductive to fast energy transfer.

In additional embodiments, TBET cassettes may be engineered to have additional properties. For example, TBET cassettes for labeling biological molecules may have groups that promote water-solubility. Groups of TBET cassettes for use in multiplexing may contain acceptors that each emit over a narrow range of wavelengths, but that are distinct from one another, thus facilitating differentiation of the cassettes' signals. TBET cassettes for use in single molecule imaging may include acceptors that do not photobleach readily. For applications that may put cassettes into general human contact, such as clothing or cosmetics, TBET cassettes may be designed to be non-toxic, particularly through skin absorption.

In certain embodiments, the TBET cassettes may be designed to have these additional properties while still meeting the criteria described above as critical for selected embodiments.

Other embodiments of the present invention include xanthine or pyronin-based donor or acceptor compounds. These compounds may have all four of the criteria described above.

Figure 1B:
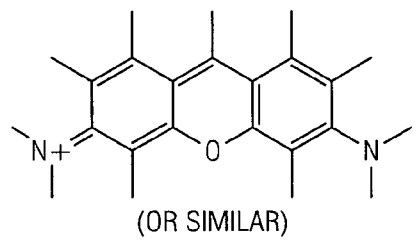
FIG. 1B illustrates pyronin-derived compounds, according to certain embodiments of the present disclosure.

FIGS. 1A and 1B shows some xanthine- or pyronin-based compounds that may be used in some embodiments of the present invention. In some cassettes, these types of compounds may be paired.

FIGS. 2A-2E illustrates some TBET cassettes, according to certain embodiments of the present disclosure. Some cassettes may include xanthine-based compounds, while others include pyronin-based compounds, or both. Some cassettes including xanthine or pyronin may be prepared according to the criteria that may be critical in some embodiments of the disclosure.

Methods used to make the TBET cassettes of the present invention may include organometallic coupling reactions. Such reactions have been determinable by one skilled in the art for some time. However, such reactions are more specifically described in: Syntheses of Regioisomerically Pure 5- or 6-Halogenated Fluoresceins, G. S. Jiao, J. W. Han, and K. Burgess, *J. Org. Chem.*, 2003, 68, 8264-8267; Fluorescent, Through-Bond Energy Transfer Cassettes for Labeling Multiple Biological Molecules In One Experiment, G. S. Jiao, L. H. Thoresen, and K. Burgess, *J. Am. Chem. Soc.*, 2003, 125, 14668-14669; Microwave-Assisted Syntheses of Regioisomerically Pure Bromorhodamin Derivatives, G. S. Jiao, J. C. Castro, L. H. Thoresen, and K. Burgess, *Org. Lett.*, 2003, 5, 3675-3677; and Microwave-assisted functionalization of bromo-fluorescein and bromorhodamine derivatives, J. W. Han, J. C. Castro, and K. Burgess, *Tetrahedron Lett.*, 2003, 44, 9359-9362.

Referring now to the specific embodiment of cassette 1 of FIG. 2, the cassette has at least two twists in a conjugated system including a xanthine-based donor and a pyronin-based acceptor. Cassette 1 also includes a linker based on a diphenylethyne fragment. A peripheral ester-alkyl-acid functional group attached to the linker may be used to connect the cassette to biological molecules.

Cassette 1 is particularly resistant to photobleaching when compared to fluoresceins because the rhodamine-like acceptor fragment is less vulnerable to decomposition in the excited state. Thus, cassette 1 may be particularly well-suited for single-molecule imaging.

Figure 2A:
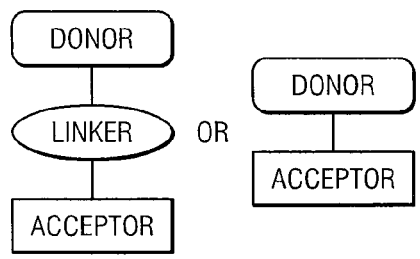
FIG. 2A illustrates a generic TBET cassette structure.
Figure 2B:
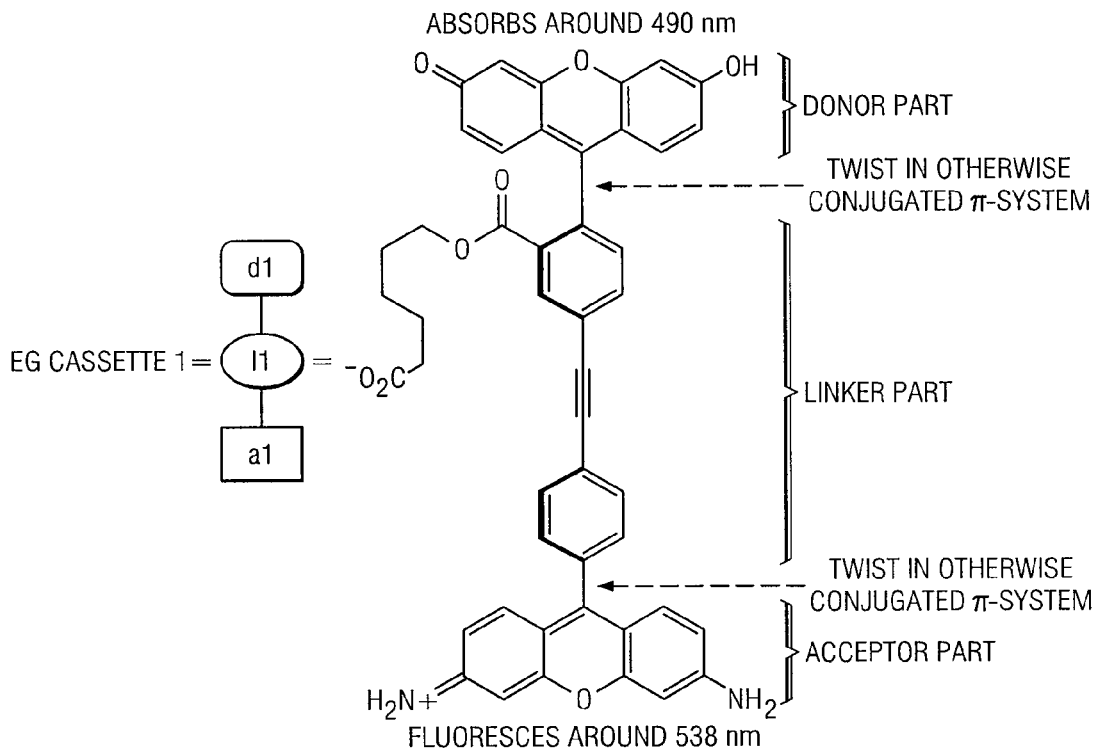
FIG. 2B illustrates cassette nomenclature for cassette 1.
Figure 2C:
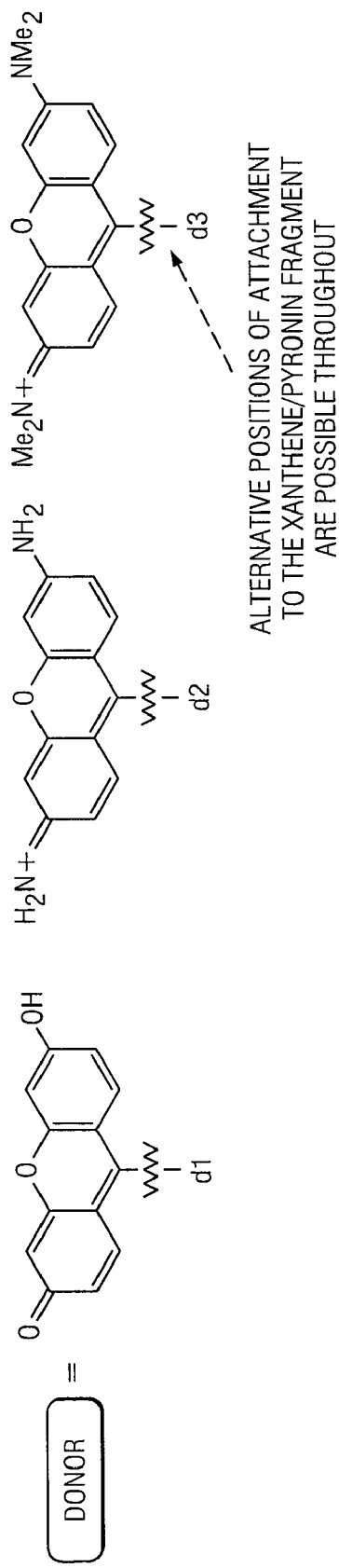
FIG. 2C illustrates selected donor groups that may be included in a TBET cassette.
Figure 2D:
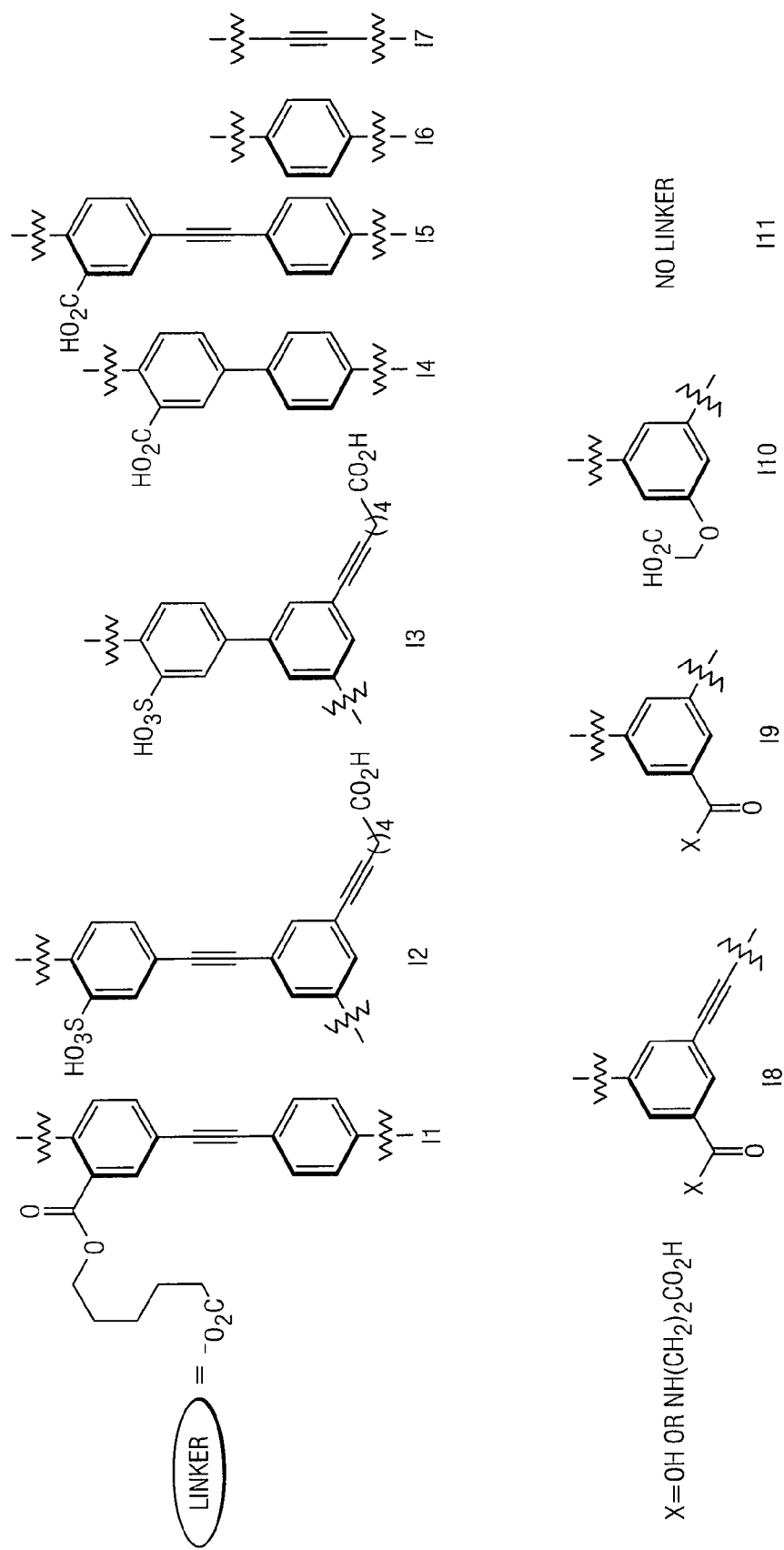
FIG. 2D illustrates selected linker groups that may be included in a TBET cassette.
Figure 2E:
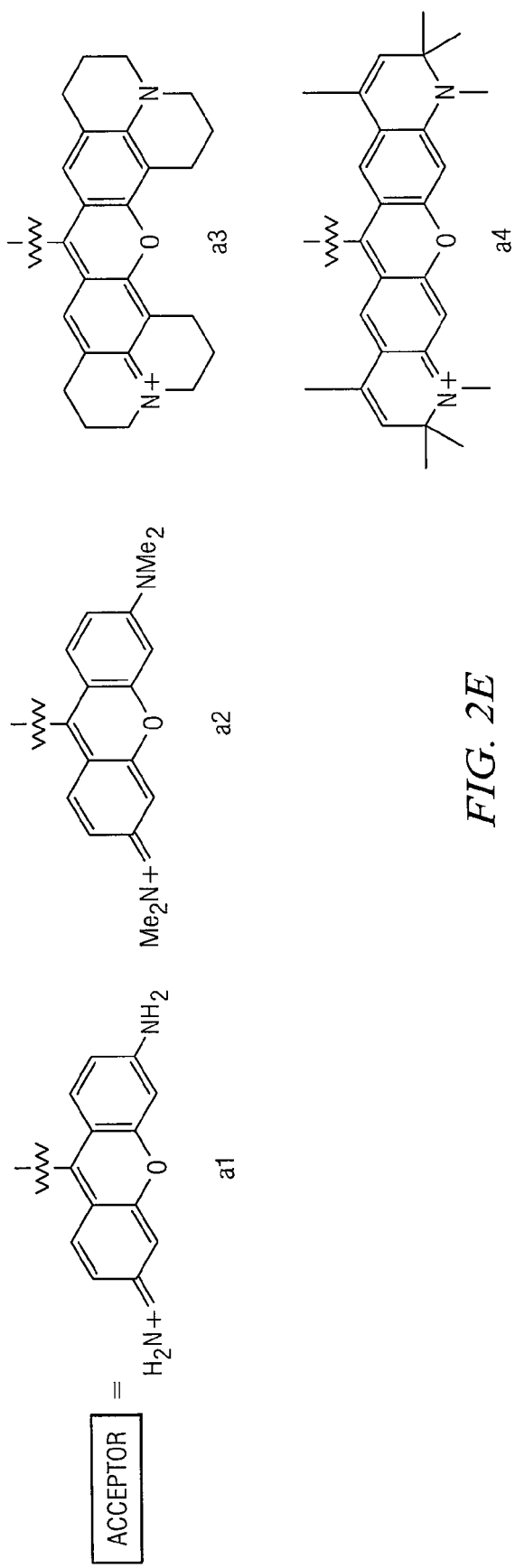
FIG. 2E illustrates selected acceptor groups that may be included in a TBET cassette.

Acceptors 1-4 of FIG. 2E may be used together for applications involving multiplexing because they have well-spaced emission wavelengths (538, 582, 603 and 616 nm in EtOH, respectively).

TBET cassettes of the present invention may be used in a variety of applications in various embodiments. For example, proteins, polypeptides, and amino acids may be labeled for proteomics, sequencing, imaging and other biochemical applications. Nucleic acids such as DNA or RNA or nucleotides may be labeled for genomics, high-throughput sequencing, and genotyping applications. In some embodiments of the invention, synthetic or non-naturally occurring nucleotides and amino acids may be labeled or included in labeled molecules.

TBET cassettes may also be put to simpler uses, such as dye coloring of clothes or cosmetics products such as hair or skin dyes or pigments. TBET cassettes may also be incorporated into new materials such as ones useful for unusual fluorescence or optical properties.

Sets of energy transfer dyes are particularly useful for applications in which several molecular entities are to be excited using the same wavelength (corresponding to the same donor in each cassette), but should ideally emit at different wavelengths (different acceptors), i.e., multiplexing. An example of this type of application are in DNA sequencing wherein one label is used in each of the four sequencing reactions. The excitation wavelength used in most contemporary DNA sequencing machines is the same, but the fluorescence emissions should be sharp, well resolved, and distinct for each label used in each experiment. Another example featuring multiplexing would be to use several TBET cassettes with the same donor to label several different proteins in a cell, excite them all simultaneously using a single wavelength excitation source, and observe distinct emission wavelengths characteristic of the labels used on each protein. In a simple example, two proteins may labeled such that, while sharing a common donor, each has a unique acceptor. Colocalization may be assessed by exposing the proteins to the excitation wavelength and monitoring the emissions from the respective acceptors.

The invention claimed is:

1. An energy transfer cassette comprising a through-bond energy transfer cassette comprising a donor and an acceptor, wherein at least one of the donor and acceptor comprises a xanthine-based or pyronin-based compound.

2. The energy transfer cassette of claim 1, further comprising a linker.

3. The transfer cassette of claim 1, further comprising the donor operable to absorb electromagnetic energy at a first wavelength and the acceptor operable to emit electromagnetic energy at a second wavelength, wherein the second wavelength is longer than the first wavelength.

4. The energy transfer cassette of claim 1, wherein the donor π-system and acceptor π-system are not n-conjugated in a ground state due to the presence of one or more twists that render the donor π-system and acceptor π-system non-planar.

5. The energy transfer cassette of claim 3, wherein the through-bond energy transfer cassette has a high molar extinction coefficient at the first wavelength.

6. The energy transfer cassette of claim 3, wherein the acceptor emits a high quantum yield at the second wavelength.

7. The energy transfer cassette of claim 3, further comprising a functional group operable to attach the cassette to a biological molecule.

8. The energy transfer cassette of claim 1, wherein the donor is selected from the group consisting of:

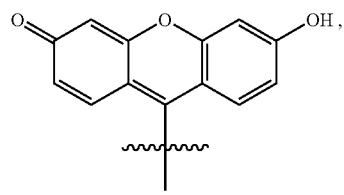

d1

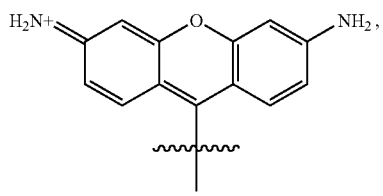

d2

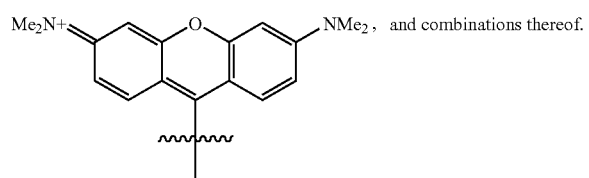

d3 and combinations thereof.

9. The energy transfer cassette of claim 1, wherein n is 1 and the linker is selected from the group consisting of:

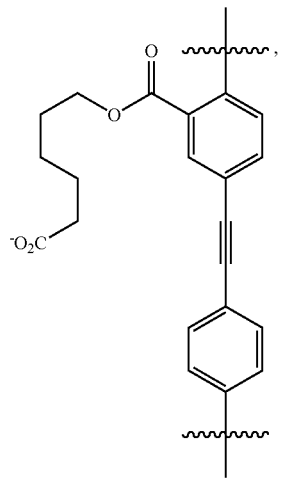

11

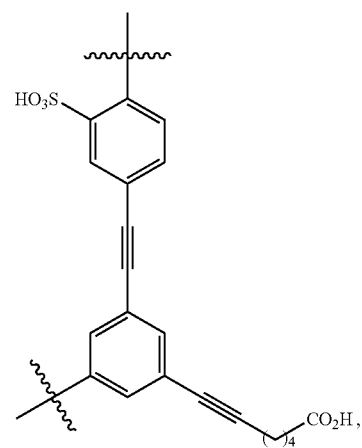

12

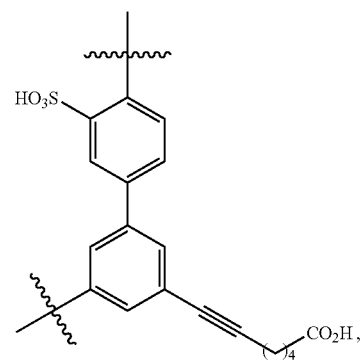

13 l4
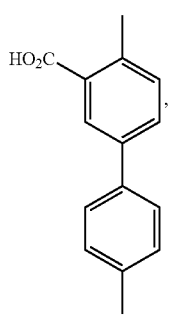
l5
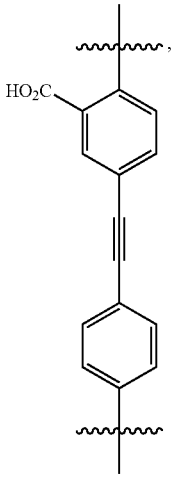
l6
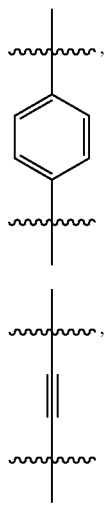
l7
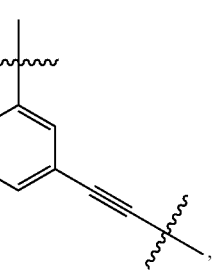
l9
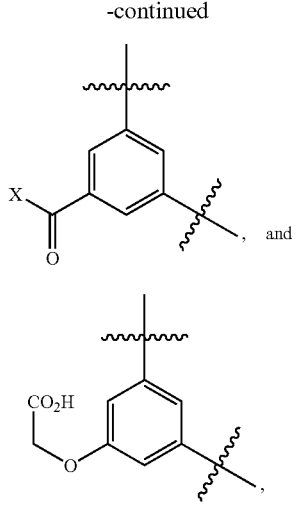, and
l10
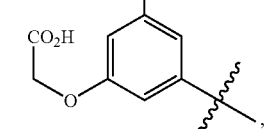,
wherein X is —OH or —NH(CH$_2$)$_2$CO$_2$H.
10. The energy transfer casseffe of claim 1, wherein the acceptor is selected from the group consisting of:
a1
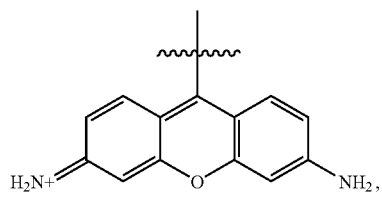
a2
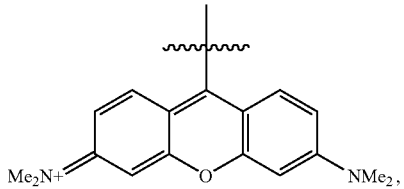
a3
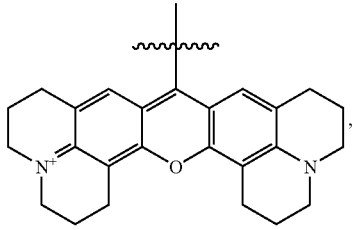
a4
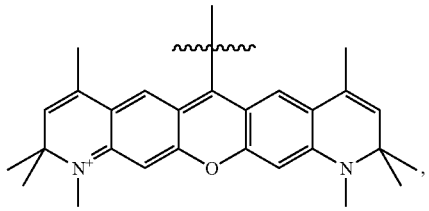
and combinations thereof.
* * * * *